United States Patent [19]

Viebach

[11] Patent Number: 5,072,723
[45] Date of Patent: Dec. 17, 1991

[54] COUPLING STRUCTURE FOR LITHOTRIPTER

[75] Inventor: Thomas Viebach, Paehl, Fed. Rep. of Germany

[73] Assignee: Dornier Medizintechtik GmbH, Munich, Fed. Rep. of Germany

[21] Appl. No.: 530,219

[22] Filed: May 30, 1990

[30] Foreign Application Priority Data

Jun. 1, 1989 [DE] Fed. Rep. of Germany ....... 3917858

[51] Int. Cl.⁵ .............................................. A61B 17/22
[52] U.S. Cl. .............................................. 128/24 EL
[58] Field of Search ............ 128/24 A, 24 EL, 660.03

[56] References Cited

U.S. PATENT DOCUMENTS

| 4,813,402 | 3/1989 | Reichenberger et al. | 128/24 EL |
| 4,858,597 | 8/1989 | Kurtze et al. | 128/24 EL |
| 4,869,230 | 9/1989 | Krauss et al. | 128/24 EL |
| 4,893,614 | 1/1990 | Takayama et al. | 128/24 EL |
| 4,920,955 | 5/1990 | Mahler et al. | 128/24 EL |

Primary Examiner—Kyle L. Howell
Assistant Examiner—K. M. Pfaffle
Attorney, Agent, or Firm—R. H. Siegemund

[57] ABSTRACT

A coupling structure in combination with a shockwave generator and either a bed or just an interface surface to the generator is made of a stiff and rigid coupling surface element being in effect interposed between the shockwave generator and a patient, the coupling surface element has no opening, but is permeable to shockwaves.

9 Claims, 2 Drawing Sheets

COUPLING STRUCTURE FOR LITHOTRIPTER

BACKGROUND OF THE INVENTION

The present invention relates to coupling a patient to a lithotripter and more particularly the invention relates to the coupling of shockwaves, generated by a a lithotripter, into the body of the patient who may rest on a particular bed or rest, or is otherwise suitably positioned for treatment.

In the past lithotripters were coupled to the body of a patient by means of water. In particular the lithotripter containing a source of shockwaves as well as facilities for focusing the shockwaves was placed in the vicinity of the body of the human beings and patient, and there was an open water bath or water cushion closed off by means of a flexible membrane for coupling the lithotripter to the body. Either the patient was submerged in a tank or a water cushion was interposed between the body of the patient and the lithotripter. There cannot be any question that such a closed water cushion is very practical in clinical practice. Disadvantages however are to be seen in the fact that this cushion, so to speak has to be operated. It has to be subjected to a very accurate pressure control and regulation. Moreover, unforseeable shifting of the patient may lead to folds in the cushion or may pose collision problems or the like.

U.S. Pat. No. 4,869,239 based on German patent 35 32 678, discloses a patient rest with a window and a water layer is provided in that window; various constructions are shown with and without covering flexible membrane. But even here any kind of pressure changes may result in undesired and unforseeable shift of the patient. It should be observed that shifting of the patient relative to the equipment has to be avoided at all costs. The equipment is positioned to establish a focus right in the concrement to be comminuted and unless the patient shifts such an out of focus situation is quite dangerous.

DESCRIPTION OF THE INVENTION

It is an object of the present invention to provide a new and improved coupling structure in conjunction with a lithotripter, which is immune against undesired touching by the patient and will no longer invite shifting of the positioning of the equipment in relation to the patient's body.

It is therefore a specific object of the invention to provide a new and improved coupling structure to be used in conjunction with extracorporally produced shockwaves such as a lithotripter and having a coupling surface through which the shockwaves can enter the body of the patient lying on the rest.

In accordance with the preferred embodiment of the present invention the object is obtained by providing the coupling surface as a stiff and rigid element which may be plane or convex facing the patient in the longitudinal direction of the patient, and concave transversely thereto though complete planarity or convexity is likewise possible. The coupling surface should be made from a uniformly thick element made of polyethylene and of synthetic with acoustical impedance similar to that of water. The coupling surface is permeable to shockwaves.

The invention therefore is based on the notion that the coupling element between the patient and a shockwave source, possibly a coupling medium thereof is to be stiff and rigid whereby stiffness within the context of the invention refers to an element which is so stiff that as a patient when placed on it, it does not change its contour, or to an extremely minimal extent only. Therefore the element is shape stable and rigid.

The coupling element is usually used in conjunction with a water bath. The lithotripter is for example freely suspended in a head whose one surface is formed by the coupling element, or the element is in fact a portion of the rest or bed on which the patient lies. The patient rests completely without being exposed to pressing edges. The patient will not be aware of any motion between him or her and the lithotripter i.e. the shockwave source. There are no forces which can displace the patient and/or the concrement in him/her and the shockwaves source. The shock wave unit can be removed and replaced by a X-ray device, still without causing a change in the relative portion of the concrement. No pressure control is necessary and there is no danger of collision of the patient with the equipment because the stiff coupling element is always interposed and, as stated, may be a component of a patient's rest or bed.

The coupling element is such that all different kinds of patients can in fact lie on it, and a large area contact with the skin is guaranteed. Body contact may be enhanced through a coupling gel or a gellike paste e.g. in so called ultrasonic areas media are used known under the trade name of Sonar Aid, or Reston, Selection criteria for the material of the stiff element are acoustical impedance, permeability to X-rays, stiffness and workability. Polyethylene has already been suggested above and is good indeed in all these cases. As stated, the shockwave source may be movably mounted below the element, within a water bath or is suspended in a pot having its upper edge sealed against the stiff coupling from below.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, a patient rest 1 has the rest surface for the body of a patient. A central portion of the rest is constructed as a stiff and rigid coupling element CE. It can be seen that the coupling element CE is three dimensionally curved and is basically of a saddle configuration. The curvature in the direction of the patient length extension L1 is convex, and concave transversely thereto. The surface L itself i.e. both ends at the coupling element CE are also concavely shaped. The coupling element can be made e.g. through deep drawing of a thermoplastic plate.

Figure 1:
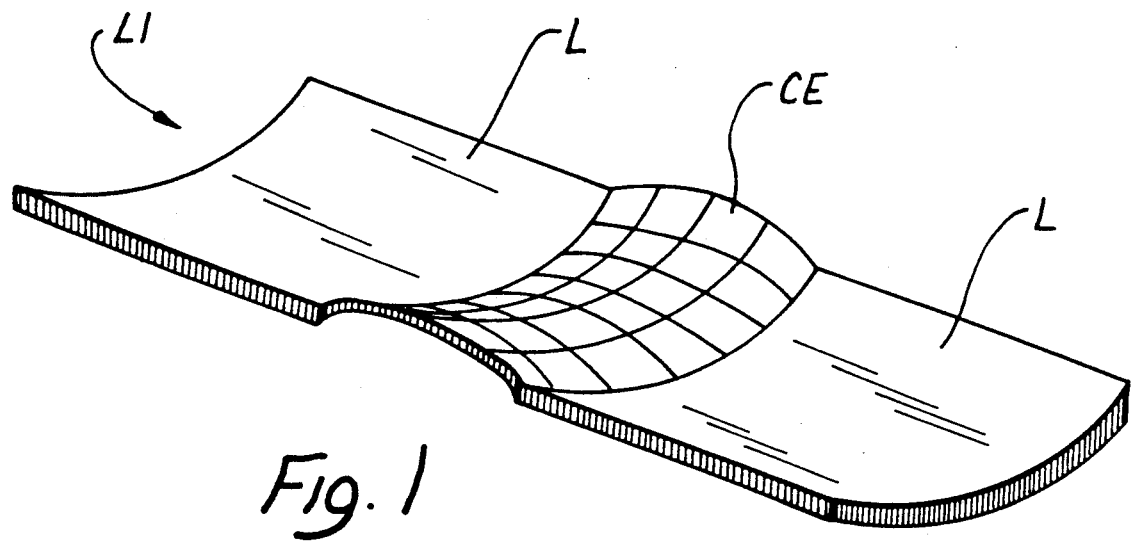
FIG. 1 illustrates a rest constructed in accordance with the preferred embodiment of the present invention for practicing a best mode configuration thereof.
Figure 2A:
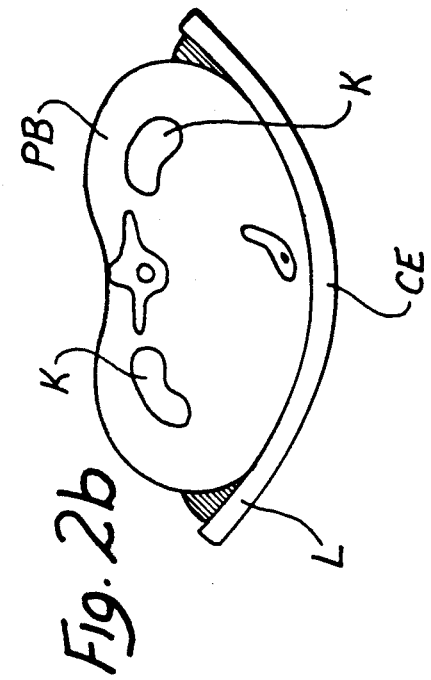
FIGS. 2a,b show two different ways of coupling, the rest of the kind shown in FIG. 1 to the body of a patient.

FIGS. 2a,b can be construed to be cross sections through the patient's rest of the kind shown in FIG. 1. FIG. 2a shows the cross section through the body PB of a patient, and shown also is a cross section through the spine SP and the kidneys K of that patient. The coupling surface element CE of the rest L is to be as rigid and stiff as possible so that inherently there is certain portion in which the coupling surface of element CE is not in contact with the body of the patient PB. These zones are filled with a coupling gel CG.

Figure 2B:
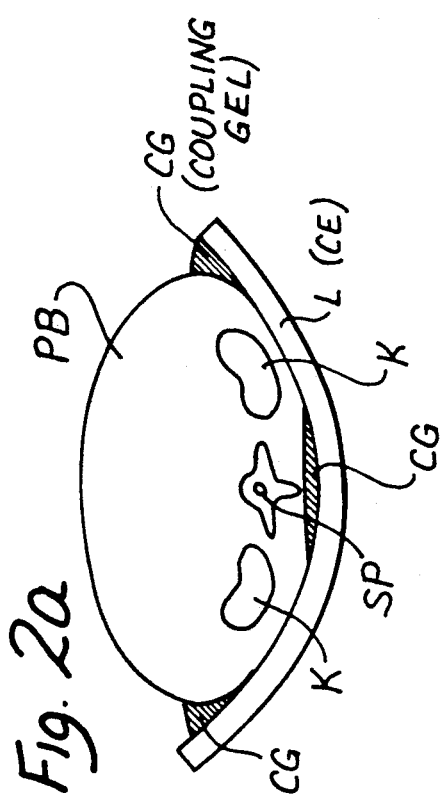

The FIG. 2b shows the same rest and same patient lies on his/her stomach. The reason is, that the contact with the convex/concave element CE will be better using less coupling gel.

Figure 3A:
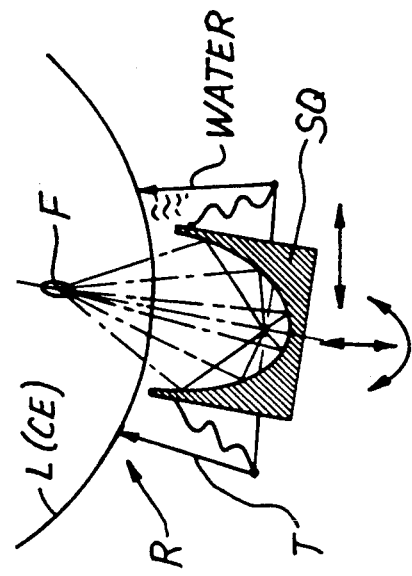
FIGS. 3a,b show the rest in conjunction with a shockwave source, the figure shown in two different ways of association.

FIG. 3a shows broadly the coupling surface element CE in conjunction with a shockwave source SQ underneath the patient's rest L. The same is shown in 3b but the two figures differ as follows. FIG. 3a illustrates also a water tank covering the entire zone underneath the coupling surface CE, and the shockwave source SQ is submerged and suspended in that water bath. The position is such that there is a focal point F of the shockwaves as produced in the source SQ. Of course a concrement is supposed to be positioned in that focal point F. The double arrows show that the source SQ in the bath is up and down, left and right, and is also rotated to thereby shift the focus vis-a-vis the patient as he or she lies on the rest L in firm contact with the rigid coupling surface element CE.

Figure 3B:
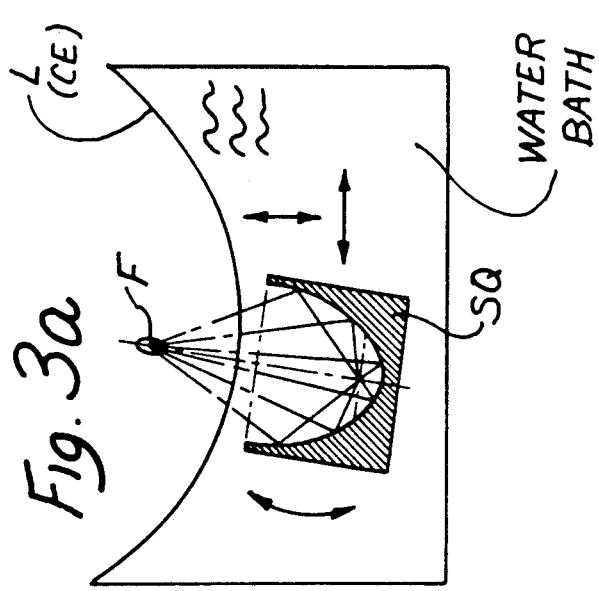

FIG. 3b shows a different arrangement wherein the source SQ is suspended inside a small container T which is placed underneath the coupling surface element CE of the rest L. The water bath for coupling the shockwave source to the patient is considerably smaller, and the upper edge of the container T seals from below against the rigid coupling surface element CE source SQ is displaceable in the container T as indicated by the various arrows to thereby shift the shockwave source vis-a-vis the rest of the patient.

Figure 4:
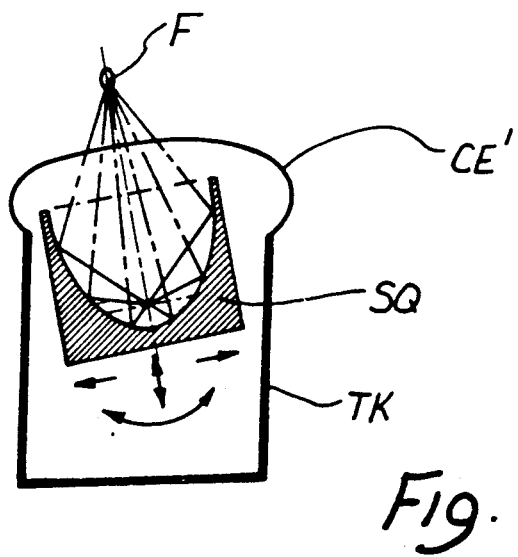
FIG. 4 is a cross-section through a therapeutic head, illustrating that the invention can be practiced without physical incorporation in a bed or rest.

FIG. 4 illustrates a therapeutic head with a coupling element CE' being still rigid and convex as shown in the plane of the drawing as well as transversly thereto. The lithotripter shockwave source SQ is movably suspended in the container TK so that also here and after coupling to the body of the patient, only the lithotripter SQ will be moved and not the coupling structure CE' in relation to the patient.

The invention is not limited to the embodiments described above but all changes and modifications thereof, not constituting departures from the spirit and scope of the invention, are intended to be included.

I claim:

1. In a lithotripter including a shockwave generator, the improvement comprising:
    a coupling structure positioned and mounted for alignment with the shockwave generator and with shockwaves generated by the shockwave generator, said coupling structure being comprised of a stiff and rigid coupling surface element, said surface element being adapted to be interposed between the shockwave generator and a patient, the coupling surface element having a particular contour and no opening, but being permeable to shockwaves, the surface element being sufficiently stiff in order to not deform when urged against the patient, but contour-adapting the patient's skin to the contour of the surface element.

2. In a lithotripter as in claim 1, the improvement including a patient rest, said rigid and stiff coupling surface element being a part of said rest, said rest having a length extension, said coupling surface element having a concavely curved contour transversely to the length extension.

3. In a lithotripter as in claim 1, the improvement wherein the rigid and stiff coupling surface element is made of polyethylene, said surface element having essentially a uniform thickness.

4. In a lithotripter as in claim 1, wherein the coupling surface element comprises a synthetic material having an acoustical impedance comparable to water.

5. In a lithotripter as in claim 1, wherein the contour is of convex configuration.

6. In a lithotripter which includes a shockwave generator with a liquid shockwave transmitting portion and a coupling structure positioned and mounted in combination with the shockwave generator, the improvement for the coupling structure comprising:
    a rigid plate structure interposed between said liquid portion of the shockwave generator and a patient, the plate being permeable to shockwaves, the plate being provided with a contour for adapting the skin of the patient to said contour of the plate.

7. In a lithotripter as in claim 6, including a patient's rest, the rigid plate being a portion of said patient's rest.

8. In lithotripter as in claim 6 further including a container said rigid plate being a cover of the container, the shockwave generator being movably mounted in that container.

9. In a lithotripter as in claim 6, the plate being convexly curved in a length direction for a patient when on the plate, and being concavely curved transversely thereto.

* * * * *